United States Patent [19]

Chen

[11] Patent Number: 5,594,002
[45] Date of Patent: Jan. 14, 1997

[54] BENZAZABICYCLIC CARBAMATES AS NOVEL CHOLINESTERASE INHIBITORS

[75] Inventor: Yuhpyng L. Chen, Waterford, Conn.

[73] Assignee: Pfizer Inc, New York, N.Y.

[21] Appl. No.: 328,205

[22] Filed: Oct. 25, 1994

Related U.S. Application Data

[62] Division of Ser. No. 835,904, filed as PCT/US89/03760 Aug. 30, 1989, published as WO91/03467 Mar. 21, 1991, Pat. No. 5,387,590.

[51] Int. Cl.⁶ .................. C07D 221/22; A61K 31/445
[52] U.S. Cl. .................................. 514/295; 546/97
[58] Field of Search .................. 546/97; 514/295

[56] References Cited

U.S. PATENT DOCUMENTS

| | | | |
|---|---|---|---|
| 2,924,603 | 2/1960 | Gordon | 514/245 |
| 3,345,373 | 10/1967 | Gordon | 514/245 |

OTHER PUBLICATIONS

Druckarach et al., Life Science, 42, 1001 (1988);.
Summers et al., *New England Journal of Medicine*, 315, 1241 (1986);.
Goodman and Gilman's *The Pharmacological Basis of Therapeutics*, 8th Ed., Pergamon Press, pp. 147 and 489–490.
Arthur E. Jacobson and Michael Mokotoff, *Azabicyclo Chemistry I. Synthesis of 1.5–Methano–7–methoxy–2,3,4, 5–tetrahydro–III–2–benzazepines. B–Norbenzomorphans*, J. Chem. Soc., (13) 7–9 (1970).
Yokoyama et al., J. Med. Chem., 22, 537 (1979).

*Primary Examiner*—Robert Gerstl
*Attorney, Agent, or Firm*—Peter C. Richardson; Paul H. Ginsburg; Garth Butterfield

[57] ABSTRACT

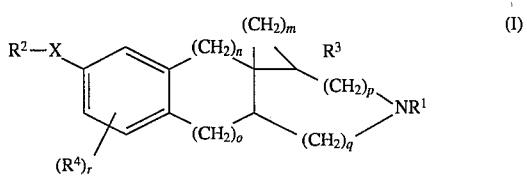

Compounds of formula (I), wherein $R^1$, $R^2$, $R^3$, $R^4$, X, m, n, o, p, q and r are as defined below. The compounds are memory enhancing cholinesterase inhibitors useful in enhancing memory, novel intermediates used in their synthesis, and analgesic agents.

5 Claims, No Drawings

BENZAZABICYCLIC CARBAMATES AS NOVEL CHOLINESTERASE INHIBITORS

This is a division, of application Ser. No. 07/835,904, filed on Feb. 28, 1992, now U.S. Pat. No. 5,387,590 which is a continuation of PCT patent application PCT/US89/03760 filed Aug. 30, 1989 which published as WO 91/03467 on Mar. 21, 1991.

BACKGROUND OF THE INVENTION

The present invention relates to benzazabicyclic carbamates of the formulae I and II below, and the pharmaceutically acceptable salts of such compounds. The compounds of formula I are cholinesterase inhibitors and are useful in enhancing memory in patients suffering from Dementia and Alzheimer's disease. The compounds of formula II are novel intermediates used in the synthesis of compounds of formula I. As set forth in detail below, the compounds of formula I and certain of the compounds of formula II are also useful as analgesic agents.

Alzheimer's disease is associated with degeneration of cholinergic neurons in the basal forebrain that play a fundamental role in cognitive functions, including memory. Becker et al., Drug Development Research, 12, 163–195 (1988). As a result of such degeneration, patients suffering from the disease exhibit a marked reduction in acetylcholine synthesis, choline acetyltransferase activity, acetylcholinesterase activity and choline uptake.

It is known that acetylcholinesterase inhibitors are effective in enhancing cholinergic activity and useful in improving the memory of Alzheimer's patients. By inhibiting acetylcholinesterase enzyme, these compounds increase the level of acetylcholine, a neurotransmitter, in the brain and thus enhance memory. Becker et al., supra, report that behavioral changes following cholinesterase inhibition appear to coincide with predicted peak levels of acetylcholine in the brain. They also discuss the efficacy of the three known acetylcholinesterase inhibitors physostigmine, metrifonate, and tetrahydroaminoacridine.

European Patent 0253372 refers to 1,2,3,3a,8,8a-hexahydro -3a,8 (and 1,3a,8) -di (and tri) methylpyrrolo/2,3-b/ indoles of the formula

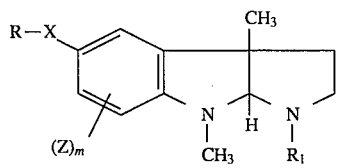

wherein R, $R_1$, X, Z, and m are as defined in such patent, and states that such compounds inhibit acetylcholinesterase are useful as memory enhancing and analgesic agents.

European Patent 0154864 refers to physostigmine derivatives of the formula

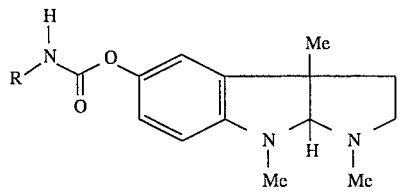

wherein R is $(C_2-C_{20})$ alkyl, branched alkyl, cycloalkyl or aryl, and states that such compounds inhibit acetylcholinesterase and are useful in the treatment of Alzheimer's disease.

Yu et al., Febs Letters, 234, 1, 127–130, (1988), refer to physostigmine derivatives of the formula

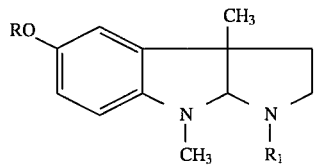

wherein R is as defined in such article, and discuss their relative potencies as inhibitors of acetylcholinesterase and butylcholinesterase as compared to the corresponding potency of physostigmine.

Atack et al., J. Pharmacology and Experimental Therapeutics, 249, 1, 194–202 (1989), refer to certain carbamoyl and N(1)-substituted analogs of physostigmine and discuss their relative potency as cholinesterase inhibitors as compared to physostigmine.

Brufani et al., Eur. J. Biochem, 157, 115–120 (1986), refer to physostigmine analogs of the formula

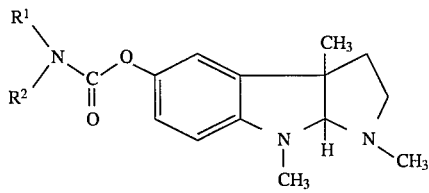

wherein $R^1$ is an alkyl group and $R^2$ is hydrogen, and state that such compounds possess anticholinesterase activity.

Known cholinesterase inhibitors are useful over a relatively small range of concentrations and exhibit adverse side effects, becoming exremely toxic at concentrations substantially higher than the effective range. Also, the relationship between cholinesterase inhibition and changes in acetylcholine concentrations that follow such inhibition has been shown to be unpredictable, not solely the result of percent cholinesterase inhibition, and strongly affected by the properties of individual drugs. There is therefore a great need for novel cholinesterase inhibitors.

SUMMARY OF THE INVENTION

The present invention relates to compounds of the formula

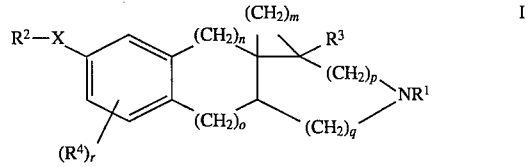

wherein each of m, n, o, q, p and r is an integer from 0 to 3;

X is O or S;

$R^1$ is hydrogen; $(C_1-C_4)$ alkyl; $(C_3-C_8)$cycloalkyl; $(C_3-C_8)$ cycloalkyl-$(C_1-C_4)$ alkyl; $(C_1-C_4)$ alkenyl-$(C_1-C_4)$ alkyl; aryl-$(C_1-C_4)$ alkyl wherein the aryl moiety is selected from the group consisting of phenyl and naphthyl, and wherein said aryl moiety may be optionally substituted with one or more substituents selected from the group consisting of $(C_1-C_4)$ alkyl, $(C_1-C_4)$ alkoxy, halogen, amino, and trifluoromethyl; or heteroaryl-$(C_1-C_4)$ alkyl wherein said heteroaryl moiety is selected from the group consisting of pyridyl, thienyl, furanyl, pyrazinyl, pyrrolyl, indolyl, pyrimidyl, and wherein said heteroaryl moiety may be optionally substituted with one or more substituents selected from the group consisting of $(C_1-C_4)$ alkyl, $(C_1-C_4)$ alkoxy, halogen, amino, and trifluoromethyl;

$R^2$ is $-CYNR^5R^6$;

Y is O or S;

$R^5$ is $(C_1-C_{12})$ alkyl; $(C_3-C_8)$ cycloalkyl; $(C_4-C_{12})$ bicycloalkyl; $(C_3-C_8)$ cycloalkenyl; aryl$(C_1-C_4)$ alkyl wherein said aryl moiety is selected from the group consisting of phenyl and naphthyl, and wherein said aryl moiety may be optionally substituted with one or more substituents independently selected from the group consisting of $(C_1-C_4)$ alkyl, $(C_1-C_4)$ alkoxy, amino, halogen and trifluoromethyl; heteroalkyl wherein the hetero atom is selected from the group consisting of N, O and S; aryl selected from the group consisting of phenyl and naphthyl; heteroaryl selected from the group consisting of pyridyl, thienyl, furanyl, pyrazinyl, pyrrolyl, indolyl and pyrimidyl; and wherein said aryl and heteroaryl groups may be optionally substituted with one or more substituents independently selected from the group consisting of $(C_1-C_4)$ alkyl, $(C_1-C_4)$ alkoxy, halogen, amino, and trifluoromethyl;

$R^6$ is hydrogen or $(C_1-C_{12})$ alkyl;

or $R^5$ and $R^6$, together with the nitrogen to which they are attached, form a heterocyclic containing group wherein the heterocyclic moiety is selected from the group consisting of 1-pyrrolidinyl, 1-piperidinyl, 4-morpholinyl, 4-thiomorpholinyl, 1-piperazinyl, and all other 3 to 12 membered azacyclic and azabicyclic moieties, and wherein said heterocyclic, azacyclic and azabicyclic moieties may be optionally substituted with one or more substituents from the group consisting of $(C_1-C_4)$ alkyl, $(C_1-C_4)$ alkoxy, halogen, trifluoromethyl, hydroxy, amino, phenyl and benzyl; aryl selected from the group consisting of phenyl and naphthyl; aryl $(C_1-C_4)$ alkyl wherein said aryl moiety is selected from phenyl and naphthyl; or heteroaryl selected from the group consisting of pyridyl, thienyl, furanyl and indolyl; and wherein said aryl moiety and aryl and heteroaryl groups may be optionally substituted with one or more substituents independently selected from the group consisting of $(C_1-C_4)$ alkyl, $(C_1-C_4)$ alkoxy, halogen, amino and trifluoromethyl;

$R^3$ is hydrogen; $(C_1-C_4)$ alkyl; $(C_1-C_4)$ alkoxy; amino; $(C_1-C_4)$ alkylamino; or (or $(C_1-C_4)$ dialkylamino;

and each $R^4$ is independently selected from the group consisting of hydrogen; nitrile; $(C_1-C_4)$ alkyl; phenyl; halogen; nitro; trifluoromethyl; $(C_1-C_4)$ alkoxy; carboxylate; hydroxy; amino; $(C_1-C_4)$ alkylcarbonyl; phenylcarbonyl; $(C_1-C_4)$ alkoxycarbonyl; aminocarbonyl; $(C_1-C_4)$ alkylaminocarbonyl; $(C_1-C_4)$ dialkylaminocarbonyl; $(C_1-C_4)$ alkylamino; $(C_1-C_4)$ dialkylamino; benzylamino; $(C_1-C_4)$ alkylbenzylamino; $(C_1-C_4)$ alkylcarbonylamino; and phenylcarbonylamino;

with the proviso that when X is O and $R^2$ is methyl, $R^3$ is not hydrogen.

The present invention also relates to novel intermediates used in the synthesis of compounds of formula I. These compounds have formula II below

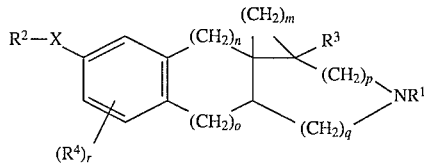

wherein $R^1$, $R^3$, $R^4$, X, m, n, o, p, q and r are as defined for formula I above, and $R^2$ is H or $(C_1-C_4)$ alkyl, with the proviso that when X is O and $R^2$ is methyl, $R^3$ is not hydrogen.

In addition to their use in synthesizing the cholinesterase inhibitors of formula I, those compounds of formula II wherein $R^2$ is hydrogen are useful as analgesic agents. The compounds of formula I are also useful as analgesic agents.

The present invention also relates to the pharmaceutically acceptable acid addition salts of compounds of the formulae I and II. Examples of such pharmaceutically acceptable acid addition salts are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, di-p-toluoyl tartaric acid, and mandelic acid.

This invention further relates to a pharmaceutical composition for inhibiting cholinesterase comprising a compound of the formula I or a pharmaceutically acceptable acid addition salt thereof, and a pharmaceutically acceptable carrier.

The invention further relates to a method for inhibiting cholinesterase in a mammal comprising administering to a mammal an amount of a compound of the formula I or a pharmaceutically acceptable acid addition salt thereof effective in inhibiting chlolinesterase.

The invention further relates to a method for enhancing memory or treating or preventing Alzheimer's disease in a mammal comprising administering to a mammal an amount of a compound of the formula I or a pharmaceutically acceptable acid addition or salt thereof effective in enhancing memory or treating or preventing Alzheimer's disease.

The invention further relates to a method for relieving, diminishing or preventing pain in a mammal comprising administering to a mammal an amount of a compound of the formula I or a pharmaceutically acceptable acid addition salt thereof effective in relieving, diminishing or preventing pain.

As used herein, the term "mammal" includes humans.

The term "$(C_1-C_4)$ alkylcarbonyl" refers to a substituent of the formula

wherein $R^7$ is $(C_1-C_4)$ alkyl.

The term "phenylcarbonyl" refers to a substituent of the formula V above wherein $R^7$ is phenyl.

The term "$(C_1-C_4)$ alkoxycarbonyl" refers to a substituent of the formula V above, wherein $R^7$ is $(C_1-C_4)$ alkoxy The term "aminocarbonyl" refers to a substituent of the formula

wherein $R^8$ and $R^9$ are both hydrogen.

The term "$(C_1-C_4)$ alkylaminocarbonyl" refers to a substituent of the formula VI above, wherein $R^8$ is $(C_1-C_4)$ alkyl and $R^9$ is hydrogen.

The term "$(C_1-C_4)$ dialkylamino" refers to a substituent of the formula VI above, wherein $R^8$ and $R^9$ are each independently $(C_1-C_4)$alkyl.

The term "$(C_1-C_4)$ alkyl amino" refers to a substituent of the formula $-NR^{10}R^{11}$ wherein $R^{10}$ is hydrogen and $R^{11}$ is $(C_1-C_4)$ alkyl.

The term "$(C_1-C_4)$ dialkylcarbonylamino" refers to a substituent of the formula $-NR^{10}R^{11}$ wherein $R^{10}$ and $R^{11}$ are each independently $(C_1-C_4)$ alkyl.

The term "benzyl amino" refers to a substituent of the formula $-NR^{10}R^{11}$, wherein $R^{10}$ is hydrogen and $R^{11}$ is benzyl.

The term "$(C_1-C_4)$ alkylbenzylamino" refers to a substituent of the formula $-NR^{10}R^{11}$, wherein $R^{10}$ is $(C_1-C_4)$ alkyl and $R^{11}$ is benzyl.

The term "$(C_1-C_4)$ alkylcarbonylamino" refers to a substituent of the formula.

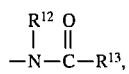

wherein $R^{12}$ is hydrogen and $R^{13}$ is $(C_1-C_4)$ alkyl.

The invention further relates to a method for relieving, diminishing or preventing pain in a mammal comprising administering to a mammal an amount of a compound of the formula II, wherein $R^2$ is hydrogen, or a pharmaceutically acceptable acid addition salt thereof effective in relieving, diminishing or preventing pain.

Preferred compounds of this invention are compounds of the formula I above, wherein X is O, $R^1$ is methyl, ethyl, propyl, or benzyl, $R^3$ is hydrogen or methyl, $R^4$ is hydrogen, Y is O, $R^5$ is n-butyl, n-propyl, n-heptyl, n-hexyl, benzyl or phenyl, $R^6$ is hydrogen, m is 1, p is 2, and each of n, o, and q is O.

Specific compounds of the invention are:
1,5-methano-3-methyl-2,3,4,5-tetrahydro-1H-3-benzazepino-7-ol-hexylcarbamate;
1,5-methano-3-methyl-2,3,4,5-tetrahydro-1H-3benzazepino-7-ol-phenylcarbamate;
1,5-methano-2-methyl-1,2,3,4,5,6-hexahydro-2-benzazacyclooctene-8-ol-heptylcarbamate,
1,5-methano-3-methyl-1,2,3,4,5,6-hexahydro-3-benzazacyclooctene-8-ol-hexylcarbamate;
1,5-ethano-3-methyl-2,3,4,5-tetrahydro-1H-3-benzazepino-7-ol-hexylcarbamate;
1,5-propano-2-methyl-2,3,4,5-tetrahydro-1H-2-benzazepino-7-ol-hexylcarbamate;
1,5-ethano-2-methyl-1,2,3,4,5,6-hexahydro-2-benzazacyclooctene-8-ol-hexylcarbamate;
1,5-methano-3-methyl-2,3,4,5-tetrahydro-1H-9-dimethylamino-3-benzazepino-7-ol-hexylcarbamate;
1,5-ethano-3-methyl-2,3,4,5-tetrahydro-1H-8-chloro-3-benzazepino-7-ol-heptylcarbamate; and
1,5-methano-2-benzyl-2,3,4,5-tetrahydro-1H-9-ethoxy-2-benzazpino-7-ol-hexylcarbamate.

The compounds of formula I have optical centers and therefore occur in different stereoisomeric configurations. The invention includes all isomers of such compounds of formula I, including mixtures thereof.

DETAILED DESCRIPTION OF THE INVENTION

The preparation of compounds of the present invention having the formulae I (e.g. IA, IB, IC, ID, ID', IE and IF) and II (e.g. IIA and IIB) are illustrated in the following reaction schemes.

Except where otherwise stated, $R^1$, $R^2$, $R^3$, $R^5$, $R^6$, X, Y, m, n, o, p, q and r in formulae IA, IB, IC, ID, ID', IE, and IF in the reaction schemes and discussion that follows are defined as they are for formula I in the "summary of the invention".

Similarly, except where otherwise stated, $R^1$, $R^2$, $R^3$, $R^5$, $R^6$, X, Y, m, n, o, p, q and r in formulas IIA and IIB in the reaction schemes and discussion that follows are defined as they are for formula II in the "summary of the invention".

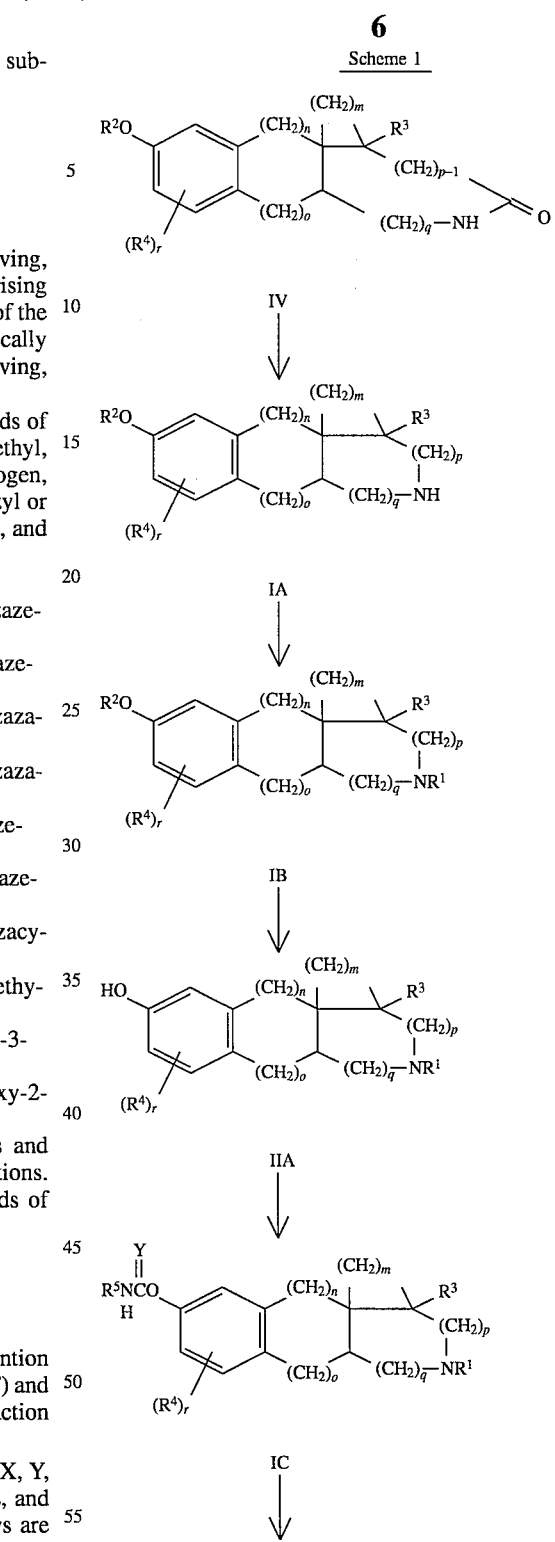

Scheme 1

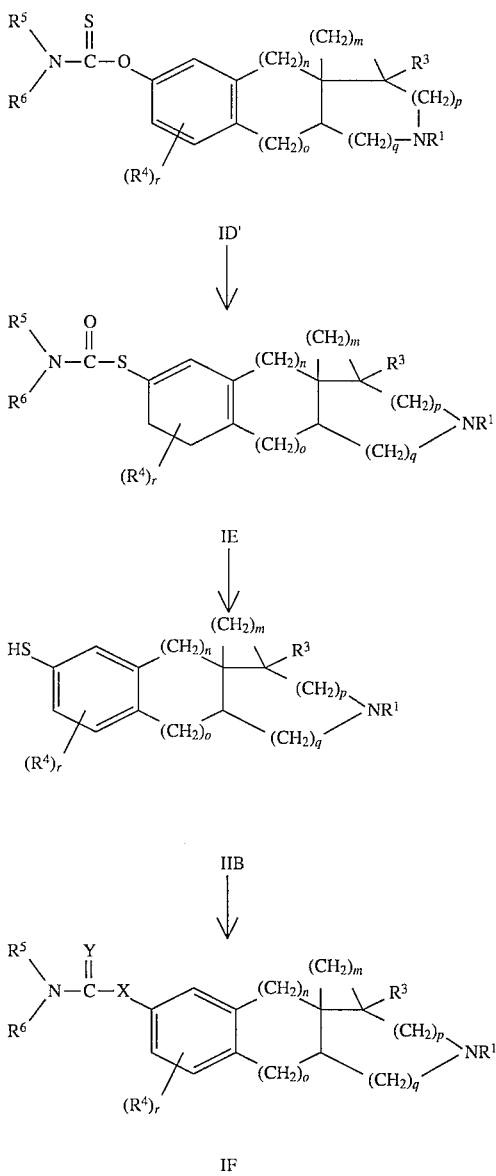

suitable solvents are toluene and ether. Suitable reaction temperatures are from about room temperature to the reflux temperature of the reaction mixture.

Compounds of the invention having the formula IB, wherein $R^2$ is $(C_1-C_4)$ alkyl and $R^4$ is hydrogen, nitrile, $(C_1-C_4)$alkyl, phenyl, halogen, nitro, trifluoromethyl or $(C_1-C_4)$alkoxy, may be prepared by reacting a compound of the formula IA, wherein $R^2$ is $(C_1-C_4)$ alkyl and $R^4$ is hydrogen, nitrile, $(C_1-C_4)$alkyl, phenyl, halogen, nitro, trifluoromethyl or $(C_1-C_4)$alkoxy, with an alkylating agent of the formula $R^1Z$, wherein Z is a leaving group such as halogen, tosylate, mesylate or triflate, in the presence of a base such as as triethylamine, potassium carbonate, dialkylamine, pyridine or sodium hydride. Dimethylformamide is the preferred solvent, but other solvents such as tetrahydrofuran and methylene chloride may also be used. The reaction is preferably carried out at about 25° C., but temperatures from about room temperature to the reflux temperature of the reaction mixture are acceptable.

Compounds of the invention having the formula IB, wherein $R^2$ is $(C_1-C_4)$ alkyl, $R^4$ is hydrogen, nitrile, $(C_1-C_4)$alkyl, phenyl, halogen, nitro, trifluoromethyl or $(C_1-C_4)$ alkoxy, and $R^1$ is not hydrogen, may be prepared alternatively from compounds of the formula IA, wherein $R^2$ is $(C_1-C_4)$ alkyl and $R^4$ is hydrogen, nitrile, $(C_1-C_4)$ alkyl, phenyl, halogen, nitro, trifluoromethyl or $(C_1-C_4)$alkoxy, by acylating such compounds of the formula IA with an acylating agent such as acetic anhydride, propionyl chloride, benzoyl chloride or acetyl chloride, and then reducing the product obtained thereby with a reducing agent such as lithium aluminum hydride or borane-dimethyl sulfide complex. The acylation step is carried out in an inert solvent such as tetrahydrofuran at a temperature from about room temperature to the reflux temperature of the reaction mixture. The reflux temperature is preferred.

Compounds of the invention having the formula IB, wherein $R^2$ is $(C_1-C_4)$ alkyl and $R^4$ is chloro, bromo or nitro, can also be obtained by reacting a compound of the formula IB, wherein $R^2$ is $(C_1-C_4)$ alkyl and $R^4$ is hydrogen, with, respectively, N-chlorosuccinamide, N-bromosuccinamide or nitronium tetrafluoroborate. Temperatures from about 0° C. to room temperature are suitable, and optimal temperatures for each reaction may be determined by monitoring the reaction using thin layer chromatography.

Compounds of the invention having the formula IIA, wherein $R^4$ is hydrogen, nitrile, $(C_1-C_4)$alkyl, phenyl, halogen, nitro, trifluoromethyl or $(C_1-C_4)$alkoxy, may be prepared by hydrolyzing compounds of the formula IB, wherein $R^2$ is $(C_1-C_4)$ alkyl and $R^4$ is hydrogen, nitrile, $(C_1-C_4)$alkyl, phenyl, halogen, nitro, trifluoromethyl or $(C_1-C_4)$alkoxy, preferably with a 48 percent solution of hydrobromic acid. Other hydrolyzing agents such as boron tribromide, aluminum trichloride and trimethylsilyl iodide in methylene chloride are also suitable. Temperatures for the hydrolysis reaction may range from about −60° C. to room temperature, with room temperature being preferred.

Compounds of the invention having the formula IC, wherein $R^4$ is hydrogen, nitrile, $(C_1-C_4)$alkyl, phenyl, halogen, nitro, trifluoromethyl or $(C_1-C_4)$ alkoxy, may be prepared by reacting a compound of the formula IIA, wherein $R^4$ is hydrogen, nitrile, $(C_1-C_4)$alkyl, phenyl, halogen, nitro, trifluoromethyl or $(C_1-C_4)$alkoxy, with a compound of the formula $R^5N=C=Y$, in the presence of a catalytic base such as sodium hydride or sodium in an aprotic solvent such as dry tetrahydrofuran, dry ether, benzene or toluene. The reaction is preferably carried out at room temperature, with Referring to Scheme 1, compounds of the invention having formula IA, wherein $R^2$ is $(C_1-C_4)$ alkyl and $R^4$ is hydrogen, nitrile, $(C_1-C_4)$alkyl, phenyl, halogen, nitro, trifluoromethyl or $(C_1-C_4)$alkoxy, may be prepared by reacting a compound of the formula IV, wherein $R^2$ is $(C_1-C_4)$ alkyl and $R^4$ is hydrogen, nitrile, $(C_1-C_4)$alkyl, phenyl, halogen, nitro, trifluoromethyl or $(C_1-C_4)$alkoxy, with a reducing agent such as lithium aluminum hydride or borane-tetrahydrofuran complex. The reaction between the compound of formula IV and the reducing agent is typically carried out in an aprotic, inert solvent such as tetrahydrofuran. Other temperatures from about 0° C. to 40° C. being acceptable. The preferred solvent is dry tetrahydrofuran and the preferred catalyst is sodium hydride.

Compounds of the invention having the formula ID, wherein $R^4$ is hydrogen, nitrile, $(C_1-C_4)$alkyl, phenyl, halogen, nitro, trifluoromethyl or $(C_1-C_4)$alkoxy, may be prepared by reacting a compound of the formula IIA, wherein $R^4$ is hydrogen, nitrile, $(C_1-C_4)$alkyl, phenyl, halogen, nitro, trifluoromethyl or $(C_1-C_4)$alkoxy, with a compound of the formula $HNR^5R^6$, in the presence of 1,1'-carbonyldiimidazole, at a temperature from about 0° C. to the reflux temperature of the reaction mixture.

Compounds of the formula ID, wherein $R^4$ is hydrogen, nitrile, $(C_1-C_4)$alkyl, phenyl, halogen, nitro, trifluoromethyl or $(C_1-C_4)$ alkoxy, can be prepared, alternatively, by reacting a compound of the formula IIA, wherein $R^4$ is hydrogen, nitrile, $(C_1-C_4)$alkyl, phenyl, halogen, nitro, trifluoromethyl or $(C_1-C_4)$alkoxy, with a compound of the formula $R^5R^6NCYCl$ in an aprotic solvent such as dry dimethylformamide in the presence of a base such as potassium carbonate or triethylamine. Other suitable solvents are methylene chloride and dry tetrahydrofuran. The reaction is typically carried out at a temperature of from about room temperature to the reflux temperature of the reaction mixture.

As illustrated in Scheme 2, compounds of the invention having the formulae IE, IIB and IF, wherein $R^4$ is hydrogen, nitrile, $(C_1-C_4)$alkyl, phenyl, halogen, nitro, trifluoromethyl or $(C_1-C_4)$ alkoxy, may be prepared in the following manner. Compounds of the formula ID', wherein $R^4$ is hydrogen, nitrile, $(C_1-C_4)$alkyl, phenyl, halogen, nitro, trifluoromethyl or $(C_1-C_4)$ alkoxy, are heated to a temperature from about 150° to about 200° C. to produce, via a rearrangement reaction, compounds of the formula IE, wherein $R^4$ is hydrogen, nitrile, $(C_1-C_4)$alkyl, phenyl, halogen, nitro, trifluoromethyl or $(C_1-C_4)$alkoxy. The compounds of formula IE so prepared are then hydrolyzed under acidic or basic conditions, for example, using sodium hydroxide in ethanol, to produce compounds of formula IIB, wherein $R^4$ is hydrogen, nitrile, $(C_1-C_4)$alkyl, phenyl, halogen, nitro, trifluoromethyl or $(C_1-C_4)$ alkoxy.

Compounds of the formula IF, wherein $R^4$ is hydrogen, nitrile, $(C_1-C_4)$alkyl, phenyl, halogen, nitro, trifluoromethyl or $(C_1-C_4)$alkoxy, may be obtained from compounds of the formula IIB, wherein $R^4$ is hydrogen, nitrile, $(C_1-C_4)$ alkyl, phenyl, halogen, nitro, trifluoromethyl or $(C_1-C_4)$alkoxy, by several alternate methods. In one method, such a compound of the formula IIB is reacted with $R^5R^6NCY$, in a dry solvent such as benzene or ether and in the presence of a base such as sodium hydride. This reaction is typically carried out at a temperature from about room temperature to 40° C., with room temperature being preferred. In a second method, such a compound of the formula IIB is reacted with $HNR^5R^6$ in the presence of 1,1'-carbonyldiimidazole in methylene chloride or dry tetrahydrofuran, at a temperature from about room temperature to about the reflux temperature of the reaction mixture. Such compounds of the formula IF can also be prepared by reacting a compound of the formula IIB, wherein $R^4$ is hydrogen, nitrile, $(C_1-C_4)$alkyl, phenyl, halogen, nitro, trifluoromethyl or $(C_1-C_4)$alkoxy, with $R^5R^6NCYCl$ in an aprotic solvent such as dry dimethylformamide in She presence of a base such as potassium carbonate or triethylamine.

Compounds of the formulae I and II, wherein $R^4$ is a carboxylic acid, may be prepared by heating the analogous compound wherein $R^4$ is nitrile to relfux with an acid (e.g., concentrated sulfuric acid or aqueous hydrochloric acid), or by heating such compound with a base (e.g., potassium hydroxide) in methanol.

Compounds of the formulae I and II, wherein $R^4$ is hydroxy, may be prepared by reacting the analogous compounds wherein $R^4$ is methoxy with concentrated hydrobromic acid at the reflux temperature of the reaction mixture, or with boron tribromide at a temperature from about −40° to 0° C. in methylene chloride or tetrahydrofuran.

Compounds of the formulae I and II, wherein $R^4$ is amino, may be prepared from the analogous compounds wherein $R^4$ is nitro by hydrogenating such nitro compounds at a pressure of about 1 to 4 arm in the presence of Raney Nickel or palladium on carbon, or by reduction methods known in the literature, (e.g. Vogel's Textbook of Practical Organic Chemistry, pp.659–663, 679, 681, 722–725, 1082, 1137 (4th ed. 1978)).

Compounds of the formulae I and II, wherein $R^4$ is $(C_1-C_4)$ alkoxycarbonyl, may be prepared by esterifying the analogous compounds wherein $R^4$ is a carboxylic acid with a $(C_1-C_4)$ alcohol under refluxing condition in the presence of a catalytic amount of an acid (e.g. gaseous hydrogen chloride, sulfuric acid or paratoluenesulfonic acid.

Compounds of the formulae I and II, wherein $R^4$ is $(C_1-C_8)$ alkylcarbonyl or phenylcarbonyl, may be prepared by reacting the analogous compounds wherein $R^4$ is $(C_1-C_4)$ alkoxycarbonyl with a Grignard reagent (e.g., $(C_1-C_4)$ alkylmagnesium bromide or phenyl magnesium bromide) at a temperature of about −78° to 0° C.

Compounds of the formulae I and II, wherein $R^4$ is $(C_1-C_4)$ alkylaminocarbonyl, $(C_1-C_4)$ dialkylaminocarbonyl or aminocarbonyl, may be prepared by reacting the analogous compounds wherein $R^4$ is a carboxylic acid with thionyl chloride at the refluxing temperature to obtain the analogous acid chlorides. The acid chlorides are then reacted with a $(C_1-C_4)$ alkylamine or $(C_1-C_4)$ dialkylamine to form compounds wherein $R^4$ is, respectively, $(C_1-C_4)$ alkylaminocarbonyl or $(C_1-C_4)$ dialkylaminocarbonyl. Alternatively, reacting the acid chlorides with ammonia yields compounds of the invention wherein $R^4$ is amino.

Compounds of the formulae I and II, wherein $R^4$ is alkylamino, dialkylamino, benzylamino or alkylbenzylamino may be prepared as follows. The analogous compounds wherein $R^4$ is amino are reacted with a $(C_1-C_4)$ aldehyde or benzaldehyde, and then reduced with sodium cyanoborohydride or sodium borohydride to give the corresponding alkylamino or benzylamino compounds. Alternatively, the analogous compounds wherein $R^4$ is amino can be reacted with an alkyl halide or benzyl halide in the presence of a base such as triethylamine, potassium carbonate, sodium hydride or Triton B. Repeating either of the above procedures starting with the alkylamino or benzylamino products thereof yields the analogous $(C_1-C_4)$ dialkylamino or alkylbenzylamino compounds.

Compounds of the formulae I and II wherein $R^4$ is $(C_1-C_4)$ alkylcarbonylamino or phenylcarbonylamino may be prepared by reacting the analogous compounds wherein $R^4$ is amino with a $(C_1-C_4)$ acyl halide, a mixed anhydride or phenacyl halide in the presence of a base.

In each of the above reactions, pressure is not critical. Pressures in the range of about 0.5 atm to 3 atm are suitable, and ambient pressure (generally, about one atmosphere) is preferred as a matter of convenience. Also, for those reactions where the preferred temperature varies with the particular compounds reacted, no preferred temperature is stated. For such reactions, preferred temperatures for particular reactants may be determined by monitoring the reaction using thin layer chromatography.

The compounds of the invention may be administered to a patient by various methods, for example, orally as capsules or tablets, parentally as a sterile solution or suspension, and in some cases, intravenously in the form of a solution. The free base compounds of the invention may be formulated and administered in the form of their pharmaceutically acceptable acid addition salts.

The daily dose of the compounds of the invention is in the range of from about 1 to 300 mg/day.

When incorporated for parenteral administration into a solution or suspension, the compounds of the invention are present in a concentration of at least 1 weight percent, and preferably between about 4–70 weight percent (based on the total weight of the unit). The parenteral dosage unit typically contains between about 5 to 100 mg of active compound(s).

Compounds of the present invention may be administered orally with an inert diluent or an edible carrier, or they may be enclosed in gelatin capsules or compressed into tablets. Such preparations should contain at least 0.5% of active compound(s), but the concentration may vary depending upon the particular form and may be from 4 to 70 weight percent (based on the total weight of the unit). The oral dosage unit typically contains between 1.0 mg to 300 mg of active compound.

The activity of the compounds of the present invention as cholinesterase inhibitors and analgesic agents may be determined by a number of standard biological or pharmacological tests. One such procedure for determining cholinesterase inhibition is described by Ellman et al. in "A New and Rapid Colorimetric Determination of Acetylcholinesterase Activity", Biochem. Pharm. 1, 88, (1961). Examples of such procedures for determining analgesic activity are the hot plate assay described in *Lab. Animal*, 7, 42 (1978), and the tail-flick and phenylquinone assays described in *J. Pharmacol. Exp. Ther.*, 175, 435 (1970) and *J. Pharmacol. Exp. Ther.*, 179, 652 (1971).

The present invention is illustrated by the following examples. It will be understood, however, that the invention is not limited to the specific details of these examples. Melting points are uncorrected. Proton nuclear magnetic resonance spectra ($^1$H NMR) and $C^{13}$ nuclear magnetic resonance spectra ($C^{13}$ NMR) were measured for solutions in deuterochloroform ($CDCl_3$) and peak positions are expressed in parts per million (ppm) downfield from tetramethylsilane (TMS). The peak shades are denoted as follows: s, singlet; d, doublet; t, triplet; q, quartet; m, multiplet; b, broad.

EXAMPLE 1

Methyl 5-methoxyl-3-methyl-1-oximinoindan-3'-acetate 8.85 g (35 mmol) Methyl 5-methoxy-3-methyl-1-indano-3-acetate in 30 ml of methanol, 40 ml $H_2O$, 3.1 g (44.6 mmol) $HONH_2 \cdot HCl$, and $NaOAc \cdot 3H_2O$ were mixed, and the mixture was refluxed for 3 hours to give 10.348 g oxime as an oil, which was purified though silica gel column chromatography to give 9.35 g of the desired oxime. $^1$HNMR($CDCl_3$) 1.4 (s,3H), 2.6 (q,2H), 3.05 ($AB_q$, 2H), 3.6 (s,3H), 3.8 (s,3H), 6.72 (d,1H), 6.82 (dd,1H), 7.6 (d,1H) ppm; $^{13}$CNMR ($CDCl_3$) 28.3, 40.9, 42.9, 45.8, 51.5, 55.5, 107.8, 114.7, 122.9, 127.3, 156.5, 160.9, 162.1, 171.5 ppm.

EXAMPLE 2

Methyl 1-amino-3-methyl-5-methoxyindan-3-acetate hydrochloride 9.35 Grams of the title compound of example 1 was dissolved in methanol, saturated with hydrogen chloride gas and hydrogenated over 2 grams of 10 percent palladium on charcoal. Removal of the solvent gave an oil which was washed with acetone to give a white solid. The white solid was recrystallized from a mixture of acetone-methanol to give 4 g of the title compound, mp. 180°–182° C. Anal. ($C_{13}H_{17}NO_3 \cdot HCl$) C,H,N., $^1$HNMR (DMSO-$d_6$) 1.4 (s,3H), 1.8 (dd,1H), 2.5 (d,2H), 2.75 (dd,1H), 3.5 (s,3H), 3.7 (s,3H), 4.7 (t,1H), 6.82 (m,2H), 7.6 (d,1H), 8.7 (brs,3H) ppm.

EXAMPLE 3

1-Amino-3-methyl-5-methoxyindan-3-acetic acid hydrochloride 4 g of the title compound of Example 2 in 2 normal hydrochloric acid was heated to reflux, stirred at that temperature for 3 hours and evaporated to give 3.7 g of white solid.

$^1$HNMR (DMSO-$d_6$) 1.24 (s,3H), 1.42 (s,3H), 1.8 (dd, 1H), 2.2 (dd,1H), 2.46 (d,1H), 2.84 (m, 1H), 3.78 (s,3H), 4.68 (t,1H), 6.8–6.95 (m,2H), 7.46 (dd,1H), 8.0–9.0 (brs, 2H) ppm.

EXAMPLE 4

1,5-Methano-3-oxo-5-methyl-7-methoxy-2,3,4,5,-tetrahydro-1H-2-benzazepine 3.6 Grams of the title compound of Example 3 was dissolved in 500 ml pyridine. 5.61 Grams 1-cyclohexyl-3-(2-morpholinoethyl) carbodimide metho-p-toluene-sulfonate was added and the mixture was stirred for 9 days. Removal of the pyridine solvent gave a residue which was washed with water, extracted with methylene chloride, and concentrated to give an orange oil. The crude residue was purified through silica gel column chromatography to give 1.1 g of white solid, top. 166°–167° C. Anal. ($C_{13}H_{15}NO_2$) C,H,N. $^1$HNMR ($CDCl_3$) 1.4 (s,3H), 2.0 (m,2H), 2.38 ($AB_q$,2H), 3.7 (s,3H), 4.3 (t,1H), 6.58 (dd,1H), 6.67 (d,1H), 7.02 (d,1H), 8.0 (m, 1H) ppm.

EXAMPLE 5

1,5-Methano-5-methyl-7-methoxy-2,3,4,5-tetrahydro-1H-2-benzazepine and its di-p-toluoyltartaric acid salt To a solution of 1.03 g of the title compound of Example 4 in dry tetrahydrofuran was added dropwise 48 ml of 1 molar borane tetrahydrofuran complex in tetrahydrofuran. The mixture was stirred at 0° C. for 1 hour, then refluxed overnight. To the cooled (0° C.) reaction mixture was added dropwise 25 ml of 6 normal hydrochloric acid. The mixture was stirred at room temperature for 1 hour, then refluxed for 1 hour. After evaporation, a white solid was obtained which was basified with water and 10 g sodium hydroxide and extracted with methylene dichloride to give 0.962 g of colorless oil. $^1$HNMR ($CDCl_3$) 1.28 (s,3H), 1.5–1.8 (m,3H), 1.96 (m,1H), 2.02 (m,1H), 2.66(dd,1H), 3.78 (s,3H), 4.12 (d,1H), 6.6 (d,1H), 6.64 (dd,1H), 7.08 (d,1H) ppm. The corresponding di-p-toluoyl-L-tartaric acid was prepared as a white solid.

EXAMPLE 6

1,5-Methano-2-ethyl-7-methoxy-2,3,4,5-tetrahydro-1H-2-benzazepine

A solution of 0.7 g (3.7 mmol) 1,5-methano-7-methoxy-2,3,4,5-tetrahydro-1H-2-benzazepine in 15 ml methylene chloride was treated with 0.38 g (3.72 mmol) acetic anhydride and 0.29 g (3.7 mol) pyridine and stirred at room temperature for 2 hours. The mixture was quenched with dilute hydrochloric acid to pH 4 and extracted with methylene dichloride. The organic layer was neutralized with saturated sodium bicarbonate, washed with brine, dried and concentrated to give 0.66 g of a yellow oil. The oil was dissolved in dry tetrahydrofuran, and then 4.3 ml of borane dimethyl sulfide complex in tetrahydrofuran was added dropwise at 0° C. The mixture was then heated to reflux for 3.5 hours. The mixture was then coo led to 0° C. and 10 ml methanol was added. After addition, the mixture was treated with 3 ml concentrated hydrochloride and stirred at room temperature overnight. The mixture was basified with 2 normal sodium hydrochloride, extracted with ether, dried and concentrated to give 0.6 g of a colorless oil. $^1$HNMR (CDCl$_3$) 1.1 (s,3H), 1.2–1.4 (m,2H), 1.8–2.4 (m,4H), 2.6 (m,1H), 3.06 (m,1H), 3.6 (m,1H), 3.78 (s,3H), 3.9 (d,1H), 6.68 (m,1H), 6.72 (m,1H), 7.02 (d,1H) ppm. $^{13}$CNMR (CDCl$_3$) 12.6, 30.1, 40.2, 44.7, 46.5, 49.5, 55.3, 62.1, 108.9, 110.5, 124.6, 131.0, 148.3, 159.5 ppm.

EXAMPLE 7

1,5-Methano-2-ethyl-5-methyl-7-methoxy-2,3,4,5-tetrahydro-1H-2-benzazepine

The title compound was prepared from 0.9 g of the title compound of Example 5 in a manner similar to that of Example 6. 0.83 Grams of an oil was obtained. $^1$HNMR (CDCl$_3$) 1.04 (t,3H), 1.2–1.4 (m,5H) 1.63–1.84 (m,3H), 1.9–2.0 (m,1H), 2.0–2.2 (m, 1H), 2.2–2.4 (m,1H), 2.57 (dd,1H), 3.72 (s,3H), 3.84 (d,1H), 6.6 (m,2H), 6.95 (m,1H) ppm.

EXAMPLE 8

1,5-Methano-2-ethyl-7-hydroxo-2,3,4,5-tetrahydro-1H-2-benzazepine

A solution of 0.6 g of the title compound of Example 6 in 48% HBr (15 ml) was heated to reflux for 4 hours, cooled and evaporated to dryness. The residue was basified to pH 9, extracted with chloroform, dried, and concentrated to give 0.43 g of a yellow oil. $^1$HNMR (CDCl$_3$) 1.1 (t,3H), 1.3–1.5 (m,2H), 1.8–2.0 (m,2H), 2.0–2.28 (m,2H), 2.28–2.45 (m,1H), 2.5–2.7 (m,1H), 3.02 (brs,1H), 3.97 (d,1H), 6.57 (dd,1H), 6.64 (s,1H), 6.97 (d,1H) ppm.

EXAMPLE 9

1,5-Methano-2-ethyl-5-methyl-7-hydroxy-2,3,4,5-tetrahydro-1H-2-benzazepine hydrogen bromide A solution of the title compound of Example 7 in 48% hydrogen bromide was heated to reflux for 4 hours, cooled and evaporated to dryness to give a solid. $^1$HNMR (D$_2$O) 1.3 (t,3H), 1.4 (s,3H), 1.65 (m,1H), 1.9–2.4 (m,4H), 1.8–2.0 (m,1H), 2.0–2.2 (m,1H), 2.2–2.4 (m, 1H) 4.7 (d, 1H), 6.85 (m, 2H), 7.4 (m, 1H) ppm.

EXAMPLE 10

1,5-Methano-2-methyl-7-hydroxy-2,3,4,5-tetrahydro-1H-9-benzazepine

The title compound was prepared from hydrolysis of 1,5-methano-2-methyl-7-methoxy-2,3,4,5-tetrahydro-1H-2-benzazapine in a manner similar to that of Example 8. $^1$HNMR (CDCl$_3$) 1.4–1.54 (m,2H), 1.9–2.04 (m,2H), 2.26 (s 3H) 2.1–2.20 (m,1H), 2.56 (dd,1H), 3.04 (m,1H), 3.78 (d,1H), 6.58 (dd, 1H), 6.64 (d,1H), 6.99 (d, 1H) ppm.

EXAMPLE 11

1,5-Methano-2-propyl-7-hydroxy-2,3.4,5-tetrahydro-1H-2-benzazepine

The title compound was prepared from hydrolysis of the title compound of Example 23 in a manner similar to that of Example 8. $^1$HNMR (CDCl$_3$) 0.9 (t,3H), 1.4–1.65 (m,4H), 1.8–2.3 (m,5H), 2.6 (m,1H), 3.0 (m,1H), 3.9 (d,1H), 6.56 (dd,1H), 6.62 (d,1H), 6.95 (d,1H) ppm.

EXAMPLE 12

1,5-Methano-2-ethyl-2,3,4,5-tetrahydro-1H-2-benzazepino-7-ol, hexylcarbamate

A solution of 3 g (1.48 mmol) of the title compound of Example 8 in 10 ml benzene was treated with 6.3 mg(0.15 mmol) sodium hydride (60 percent in oil) and stirred for 15 minutes. 0.282 Grams (2.22 mmol) hexyl isocyanate was added and the resulting mixture was stirred at room temperature for 3 hours, quenched with brine, extracted with chloroform, dried, and concentrated to give crude product. The material was purified using 5 percent methanol in chloroform as eluent to give an oil. $^1$HNMR (CDCl$_3$) 0.85 (t,3H), 1.1 (t,3H) 1.2–1.5 (m,10H), 1.9–2.1 (m,2H), 2.1–2.3 (m, 2H) 2.3–2.5 (m,1H), 2.6 (m,1H), 3.18 (brs,1H), 3.2 (q,2H) 3.94 (d,1H), 5.21 (brs,1H), 6.88 (dd,1H), 6.94 (d,1H ), 7.06 (d,1H) ppm. The corresponding di-p-toluoyl-L-tartaric acid salt was prepared as a white solid.

EXAMPLE 13

1,5-Methano-2-ethyl-2,3,4,5-tetrahydro-1H-2-benzazepino-7-ol, heptylcarbamate

The title compound was prepared as an oil from the title compound of Example 8 in a manner similar to that described in Example 12, but using 1 equivalent heptyl isocyanate instead of hexyl isocyanate. $^1$HNMR (CDCl$_3$) 0.92 (t,3H), 1.15 (t,3H), 1.24–1.5 (m,9H), 1.5–1.7 (m,3H), 1.94–2.12 (m,2H), 2.12–2.34 (m,2H), 2.34–2.5 (m,1H), 2.68 (dd,1H), 3.16 (brs,1H), 3.3 (q,2H), 4.0 (d,1H), 5.02 (brs,1H, NH), 6.94 (dd,1H), 7.0 (d,1H), 7.1 (d,11H) ppm. The corresponding di-p-toluoyl-L-tartaric acid was prepared as a white solid.

EXAMPLE 14

1,5-Methano-2-ethyl-5-methyl-2,3,4,5-tetrahydro-1H-2-benzazepine-7-ol, hexylcarbamate The title compound was prepared by reacting the title compound of Example 9 with 1.1 equivalents of sodium hydride and 1.0 equivalents of hexyl isocyanate, using a procedure similar to that of Example 12. $^1$HNMR (CDCl$_3$) 0.8 (t,3H), 1.06 (t,3H), 1.1–1.4 (m,11H), 1.4–1.6 (m,2H), 1.6–1.9 (m,2H), 1.9–2.0 (m, 1H), 2.0–2.2 (m,1H), 2.2–2.4 (m,1H), 2.5–2.7 (m,2H), 3.15 (q,2H), 3.9 (d,1H), 5.24 (t,1H,NH), 6.8–6.9 (m,2H), 7.0 (d,1H) ppm; $^{13}$CNMR (CDCl$_3$) 12.7, 16.0, 22.65, 22.53, 26.4, 29.8, 31.5, 37.1, 41.3, 43.7, 47.2, 49.3, 51.2, 61.8, 114.5, 118.9, 124.4, 135.5, 150.8, 151.06, 154.8 ppm. The corresponding di-p-toluoyl-L-tartaric acid salt was prepared as a white solid.

EXAMPLE 15

1,5-Methano-2-ethyl-5-methyl-2,3,4,5-tetrahydro-1H-2-benzazepine-7-ol, heptylcarbamate The title compound was prepared in a manner similar to that of Example 14, but using heptyl isocyanate instead of hexyl isocyanate. $^1$HNMR (CDCl$_3$) 0.83 (t,3H), 1.08 (t,3H), 1.2–1.6 (m,15H), 1.7–1.9(m, 2H) 19–2.0 (m 1H), 2.04–2.24 (m 1H) 2.24–2.4 (m,1H), 2.5–2.7 (m,1H), 3.2 (q,H), 3.9 (d,1H), 5.13 (t,1H, NH), 6.8–6.9 (m,2H), 7.0 (d,1H) ppm. The corresponding di-p-toluoyl-L-tartaric acid salt was prepared as a white solid.

EXAMPLE 16

1,5-Methano-2-ethyl-2,3,4,5-tetrahydro-1H-2-benzazepino-7-ol, butylcarbamate

The title compound was prepared as an oil by a procedure similar to that of Example 12 but using 1 equivalent of n-butyl isocyanate instead of hexyl isocyanate. $^1$HNMR (CDCl$_3$) 0.94 (t,3H), 1.1 (t,3H), 1.3–1.46 (m,3H), 1.46–1.6 (m,3H), 1.9–2.04 (m,2H), 2.04–2.28 (m,2H), 2.28–2.42 (m,1H), 2.64 (dd,1H), 3.1 (s,1H), 3.25 (q,2H), 3.96 (d,1H), 4.98 (brs, 1H), 6.9 (d,1H), 6.96 (s,1H), 7.06 (d,1H) ppm. The corresponding di-p-toluoyl-L-tartaric acid salt was prepared in 2-propanol and concentrated to dryness to give an off-white solid which was washed with ether to give a white solid.

EXAMPLE 17

1,5-Methano-2-ethyl-2,3,4,5-tetrahydro-1H-2-benzazepino-7-ol, propylcarbamate

The title compound was prepared as an oil by a procedure similar to that of Example 12, but using 1 equivalent of n-propyl isocyanate instead of hexyl isocyanate. $^1$HNMR (CDCl$_3$) 0.9 (t,3H), 1.04 (t,3H), 1.2–1.6 (m,4H), 1.8–2.0 (m,2H), 2.0–2.4 (m,3H), 2.4–2.62 (m,1H), 2.94–3.24 (m,3H), 3.8–3.9 (m,1H), 4.92 (brs,1H), 6.7–6.9 (m,2H), 6.9–7.0 (m,1H) ppm. The corresponding di-p-toluoyl-L-tartaric acid salt was prepared as a white solid.

EXAMPLE 18

1,5-Methano-2-ethyl-2,3,4,5-tetrahydro-1H-2-benzazepino-7-ol, methylcarbamate

The title compound was prepared as an oil by a procedure similar to that of Example 12, but using 1 equivalent of methyl isocyanate instead of hexyl isocyanate. $^1$HNMR (CDCl$_3$) 1.1 (t,3H), 1.3–1.6 (m,2H), 1.85–2.1 (m,2H), 2.1–2.3 (m,2H), 2.3–2.5 (m,1H), 2.6–2.8 (m,1H), 2.9 (d,3H), 3.1 (brs,1H), 3.97 (d,1H), 4.96 (brs,1H), 6.8–7.0 (m,2H), 7.06 (d,1H) ppm. The corresponding di-p-toluoyl-L-tartaric acid salt was prepared as a white solid.

EXAMPLE 19

1,5-Methano-2-ethyl-2,3,4,5-tetrahydro-1H-2-benzazepino-7-ol, phenyl carbamate

The title compound was prepared as crystals by a procedure similar to that of Example 12, but using 1 equivalent of phenyl isocyanate instead of hexyl isocyanate. $^1$HNMR (CDCl$_3$) 1.07 (t,3H), 1.3–1.5 (m,2H), 1.9–20 (m,2H), 2.1–2.4 (m,3H), 2.65 (dd,1H), 3.06 (m,1H), 3.96 (d,1H), 6.9–7.1 (m,4H), 7.2–7.4 (m,4H) ppm. The corresponding di-p-toluyl-L-tartaric acid salt was prepared as a white solid.

EXAMPLE 20

1,5-Methano-2-methyl-2,3,4,5-tetrahydro-1H-2-benzazepino-7-ol, hexylcarbamate

The title compound was prepared as an oil by a procedure similar to that of Example 12, from 1 equivalent of the title compound of Example 10, and using 1 equivalent of n-hexyl isocyanate in the presence of 0.1 equivalents of sodium hydride. $^1$HNMR (CDCl$_3$) 0.89 (t,3H), 1.2–1.6 (m,10H), 1.86–2.0 (m,2H), 2.14 (s,3H), 2.2 (m, 1H), 2.5 (dd,1H), 3.08 (brs, W$_{1/2}$=10 Hz) 3.24 (q,2H), 3.77 (d,1H), 6.92 (dd,1H), 6.96 (d,1H), 7.1 (d,1H) ppm. The corresponding di-p-toluoyl-L-tartrate was prepared as an off-white solid.

EXAMPLE 21

1,5-Methanol-2-methyl-2,3,4,5-tetrahydro-1H-2-benzazepino-7-ol, heptylcarbamate

The title compound was prepared as an oil in a similar manner to that of Example 19, but using 1 equivalent n-heptyl isocyanate instead of n-hexyl isocyanate. $^1$HNMR (CDCl$_3$ 0.8 (t,3H), 1.1–1.6 (m,12H), 1.8–2.0 (m,2H), 2.08 (s,3H), 2.1–2.2 (m,1H), 2.46 (dd,1H), 3.03 (brs,1H), 3.18 (q,2H), 3.7 (d,1H), 4.92 (brs, 1H), 6.85 (dd, 1H), 6.9 (d,1H), 7.04 (d,1H) ppm. The corresponding di-p-toluoyl-L-tartarate was prepared in 2-propanol and concentrated to dryness. The solid was washed with ether to give an off-white solid.

EXAMPLE 22

1,5-Methano-2-propyl-2,3,4,5-tetrahydro-1H-benzazepino-7-ol, hexylcarbamate (21)

The title compound was prepared as an oil by a procedure similar to that of Example 12, from 1 equivalent of the title compound of Example 11, using 1 equivalent of n-hexyl isocyanate in the presence of 0.1 equivalents of sodium hydride. $^1$HNMR (CDCl$_3$) 0.9 (m,6H), 1.2–1.8 (m,12H), 1.9–2.4 (m,5H), 2.75 (m,1H), 3.15 (m,1H), 3.25 (q,2H), 4.0 (brs,1H), 5.0 (t,1H,NH), 6.9 (dd,1H), 7.0 (d,1H), 7.15 (d,1H) ppm. The corresponding di-p-toluoyl-L-tartaric acid salt was prepared as a white solid.

EXAMPLE 23

1,5-Methano-2-propyl-2,3,4,5-tetrahydro-1H-2-benzazepino-7-ol, heptylcarbamate (22)

The title compound was prepared as an oil in a manner similar to that of Example 21, but using 1 equivalent n-heptyl isocyanate instead of n-hexyl isocyanate. $^1$HNMR (CDCl$_3$) 0.9 (m,6H) 1.15–1.7 (m,14H), 1.9–2.35 (m,5H), 2.65 (dd,1H), 3.1 (brs,1H), 3.25 (q,2H), 3.95 (d,1H), 5.0 (t,1H),NH), 6.9 (dd, 1H), 6.98 (d,1H), 7.1 (d,1H) ppm. The corresponding di-p-toluoyl-L-tartaric acid salt was prepared as a white solid.

EXAMPLE 24

1,5 Methano-2-propyl-7-methoxy-2,3,4,5-tetrahydro-1H-2-benzazepine

2 Grams of 1,5-methano-7-methoxy-2,3,4,5-tetra-hydro-1H-2-benzazepine was reacted with 0.98 g propionyl and 0.84 g pyridine in methylene dichloride using a procedure similar to that of Example 6. $^1$HNMR (CDCl$_3$) 0.88 (t,3H), 1.2–1.6 (m,4H), 1.8–2.4 (m,5H), 2.6 (dd, 1H), 3.04 (brs,1H), 3.78 (s,3H), 3.9 (d, 1H), 6.66 (dd,1H), 6.74 (d,1H), 7.02 (d,1H) ppm.

I claim:

1. A compound of the formula

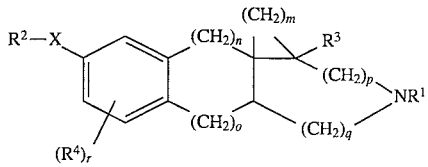

wherein each of n, o and q is zero;

m is one;.

p is two;

X is oxygen or sulfur;

$R^1$ is hydrogen; $(C_1-C_4)$ alkyl; $(C_3-C_8)$cycloalkyl; $(C_3-C_8)$ cycloalkyl-$(C_1-C_4)$ alkyl; $(C_1-C_4)$ alkenyl-$(C_1-C_4)$ alkyl; aryl-$(C_1-C_4)$ alkyl wherein the aryl moiety is selected from the group consisting of phenyl and naphthyl, and wherein said aryl moiety may be optionally substituted with one or more substituents selected from the group consisting of $(C_1-C_4)$ alkyl, $(C_1-C_4)$ alkoxy, halogen, amino, and trifluoromethyl; or heteroaryl-$(C_1-C_4)$ alkyl wherein said heteroaryl moiety is selected from the group consisting of pyridyl, thienyl, furanyl, pyrazinyl, pyrrolyl, indolyl, pyrimidyl, and wherein said heteroaryl moiety may be optionally substituted with one or more substituents selected from the group consisting of $(C_1-C_4)$ alkyl, $(C_1-C_4)$ alkoxy, halogen, amino, and trifluoromethyl;

$R^2$ is —$CYNR^5R^6$;

Y is oxygen or sulfur;

$R^5$ is $(C_1-C_{12})$ alkyl; $(C_3-C_8)$ cycloalkyl; $(C_4-C_{12})$ bicycloalkyl; $(C_3-C_8)$ cycloalkenyl; aryl; $(C_1-C_4)$ alkyl wherein said aryl moiety is selected from the group consisting of phenyl and naphthyl, and wherein said aryl moiety may be optionally substituted with one or more substituents independently selected from the group consisting of $(C_1-C_4)$ alkyl, $(C_1-C_4)$ alkoxy, amino, halogen and trifluoromethyl; heteroalkyl wherein the hetero atom is selected from the group consisting of nitrogen, oxygen and sulfur; aryl selected from the group consisting of phenyl and naphthyl; heteroaryl selected from the group consisting of pyridyl, thienyl, furanyl, pyrazinyl, pyrrolyl, indolyl and pyrimidyl; and wherein said aryl and heteroaryl groups may be optionally substituted with one or more substituents independently selected from the group consisting of $(C_1-C_4)$ alkyl, $(C_1-C_4)$ alkoxy, halogen, amino, and trifluoromethyl;

$R^6$ is hydrogen or $(C_1-C_{12})$ alkyl;

or $R^5$ and $R^6$, together with the nitrogen to which they are attached, form a heterocyclic containing group wherein the heterocyclic moiety is selected from the group consisting of 1-pyrrolidinyl, 1-piperidinyl, 4-morpholinyl, 4-thiomorpholinyl, 1-piperazinyl, and all other 3 to 12 membered azacyclic and azabicyclic moieties, and wherein said heterocyclic, azacyclic and azabicyclic moieties may be optionally substituted with one or more substituents from the group consisting of $(C_1-C_4)$ alkyl, $(C_1-C_4)$ alkoxy, halogen, trifluoromethyl, hydroxy, amino, phenyl and benzyl; aryl selected from the group consisting of phenyl and naphthyl; aryl $(C_1-C_4)$ alkyl wherein said aryl moiety is selected from phenyl and naphthyl, or heteroaryl selected from the group consisting of pyridyl, thienyl, furanyl and indolyl; and wherein said aryl moiety and aryl and heteroaryl groups may be optionally substituted with one or more substituents independently selected from the group consisting of $(C_1-C_4)$ alkyl, $(C_1-C_4)$ alkoxy, halogen, amino and trifluoromethyl;

$R^3$ is hydrogen; $(C_1-C_4)$alkyl; $(C_1-C_4)$ alkoxy; amino; $(C_1-C_4$ alkylamino; or $(C_1-C_4)$ dialkylamino;

and each $R^4$ is independently selected from the group consisting of hydrogen; nitrile; $(C_1-C_4)$ alkyl; phenyl; halogen; nitro; trifluoromethyl; $(C_1-C_4)$ alkoxy; carboxylate; hydroxy; amino; $(C_1-C_4)$alkylcarbonyl; phenylcarbonyl; $(C_1-C_4)$ alkoxycarbonyl; aminocarbonyl; $(C_1-C_4)$ alkylaminocarbonyl; $(C_1-C_4)$ dialkylaminocarbonyl; $(C_1-C_4)$ alkylamino; $(C_1-C_4)$ dialkylamino; benzylamino; $(C_1-C_4)$ alkylbenzylamino; $(C_1-C_4)$ alkylcarbonylamino; and phenylcarbonylamino;

and the pharmaceutically acceptable salts of such compounds.

2. A compound of the formula

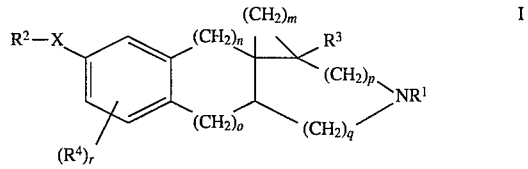

wherein each of n, o and q is zero;

m is one;

p is two;

X is oxygen or sulfur;

$R^1$ is hydrogen; $(C_1-C_4)$ alkyl; $(C_3-C_8)$cycloalkyl; $(C_3-C_8)$ cycloalkyl-$(C_1-C_4)$ alkyl; $(C_1-C_4)$ alkenyl-$(C_1-C_4)$ alkyl; aryl-$(C_1-C_4)$ alkyl wherein the aryl moiety is selected from the group consisting of phenyl and naphthyl, and wherein said aryl moiety may be optionally substituted with one or more substituents selected from the group consisting of $(C_1-C_4)$ alkyl, $(C_1-C_4)$ alkoxy, halogen, amino, and trifluoromethyl; or heteroaryl-$(C_1-C_4)$ alkyl wherein said heteroaryl moiety is selected from the group consisting of pyridyl, thienyl, furanyl, pyrazinyl, pyrrolyl, indolyl, pyrimidyl, and wherein said heteroaryl moiety may be optionally substituted with one or more substituents selected from the group consisting of $(C_1-C_4)$ alkyl, $(C_1-C_4)$ alkoxy, halogen, amino, and trifluoromethyl;

$R^2$ is hydrogen or $(C_1-C_4)$ alkyl;

$R^5$ is $(C_1-C_{12})$ alkyl; $(C_1-C_8)$ cycloalkyl; $(C_1-C_{12})$ bicycloalkyl; $(C_3-C_8)$ cycloalkenyl; aryl; $(C_1-C_4)$ alkyl wherein said aryl moiety is selected from the group consisting of phenyl and naphthyl, and wherein said aryl moiety may be optionally substituted with one or more substituents independently selected from the group consisting of $(C_1-C_4)$ alkyl, $(C_1-C_4)$ alkoxy, amino, halogen and trifluoromethyl; heteroalkyl wherein the hetero atom is selected from the group consisting of nitrogen, oxygen and sulfur; aryl selected from the group consisting of phenyl and naphthyl; heteroaryl selected from the group consisting of pyridyl, thienyl, furanyl, pyrazinyl, pyrrolyl, indolyl and pyrimidyl; and wherein said aryl and heteroaryl groups may be optionally substituted with one or more substituents independently selected from the group consisting of $(C_1-C_4)$ alkyl, $(C_1-C_4)$ alkoxy, halogen, amino, and trifluoromethyl;

$R^6$ is hydrogen or $(C_1-C_{12})$ alkyl;

or $R^5$ and $R^6$, together with the nitrogen to which they are attached, form a heterocyclic containing group wherein the heterocyclic moiety is selected from the group consisting of 1-pyrrolidinyl, 1-piperidinyl, 4-morpholinyl, 4-thiomorpholinyl, 1-piperazinyl, and all other 3 to 12 membered azacyclic and azabicyclic moieties, and wherein said heterocyclic, azacyclic and azabicyclic moieties may be optionally substituted with one or more substituents from the group consisting of $(C_1-C_4)$ alkyl, $(C_1-C_4)$ alkoxy, halogen, trifluoromethyl, hydroxy, amino, phenyl and benzyl; aryl selected from the group consisting of phenyl and naphthyl; aryl $(C_1-C_4)$ alkyl wherein said aryl moiety is selected from phenyl and naphthyl, or heteroaryl selected from the group consisting of pyridyl, thienyl, furanyl and indolyl; and wherein said aryl moiety and aryl and heteroaryl groups may be optionally substituted with one or more substituents independently selected from the group consisting of $(C_1-C_4)$ alkyl, $(C_1-C_4)$ alkoxy, halogen, amino and trifluoromethyl;

$R^3$ is hydrogen; $(C_1-C_4)$ alkyl; $(C_1-C_4)$ alkoxy; amino; $(C_1-C_4$ alkylamino; or $(C_1-C_4)$ dialkylamino;

and each $R^4$ is independently selected from the group consisting of hydrogen; nitrile; $(C_1-C_4)$ alkyl; phenyl; halogen; nitro; trifluoromethyl; $(C_1-C_4)$ alkoxy; carboxylate; hydroxy; amino; $(C_1-C_4)$ alkylcarbonyl; phenylcarbonyl; $(C_1-C_4)$ alkoxycarbonyl; aminocarbonyl; $(C_1-C_4)$ alkylaminocarbonyl; $(C_1-C_4)$ dialkylaminocarbonyl; $(C_1-C_4)$ alkylamino; $(C_1-C_4)$ dialkylamino; benzylamino; $(C_1-C_4)$ alkylbenzylamino; $(C_1-C_4)$ alkylcarbonylamino; and phenylcarbonylamino;

with the proviso that when X is oxygen and $R^2$ is methyl, $R^3$ is not hydrogen;

and the pharmaceutically acceptable salts of such compounds.

3. A pharmaceutical composition for relieving diminishing or preventing pain in a mammal, comprising a compound according to claim 1 or a pharmaceutically acceptable salt thereof, and a pharmaceutically acceptable carrier.

4. A pharmaceutical composition for enhancing memory or treating or preventing Alzheimer's disease comprising a compound according to claim 1 or a pharmaceutically acceptable salt thereof, and a pharmaceutically acceptable carrier.

5. A pharmaceutical composition for inhibiting cholinesterase in a mammal, comprising a compound according to claim 1, or a pharmaceutically acceptable salt thereof, and a pharmaceutically acceptable carrier.

* * * * *